United States Patent [19]

Dombrowski et al.

[11] Patent Number: 4,959,056
[45] Date of Patent: Sep. 25, 1990

[54] DIGITAL DISPENSER

[75] Inventors: Mitchell Dombrowski, Grosse Pointe Farms; Robert Welch, Plymouth, both of Mich.

[73] Assignee: Wayne State University, Detroit, Mich.

[21] Appl. No.: 206,607

[22] Filed: Jun. 14, 1988

[51] Int. Cl.⁵ .............................................. A61M 5/00
[52] U.S. Cl. ..................................... 604/186; 604/211
[58] Field of Search ............... 604/135, 207, 211, 130, 604/152, 186

[56] References Cited

U.S. PATENT DOCUMENTS

| | | | |
|---|---|---|---|
| 2,644,450 | 7/1953 | Krewson | 604/186 X |
| 3,279,653 | 12/1964 | Pfleger | 222/70 |
| 3,833,030 | 9/1974 | Waldbauder, Jr. et al. | 604/186 X |
| 3,859,859 | 1/1975 | Stickney | 74/2 |
| 3,985,133 | 10/1976 | Jenkins et al. | 604/67 |
| 4,177,810 | 12/1979 | Gourlandt | 604/144 |
| 4,244,366 | 1/1981 | Raines | 128/218 PA |
| 4,313,439 | 2/1982 | Babb et al. | 128/214 F |

Primary Examiner—John D. Yasko
Assistant Examiner—Adam J. Cermak
Attorney, Agent, or Firm—Reising, Ethington, Barnard, Perry & Milton

[57] ABSTRACT

A digital dispenser aid device (10) of the type for use with a syringe (12) includes a housing (24). The syringe (12) can be fixedly mounted within a chamber (28) within the housing (24). A body member 54 includes a recessed portion (56) retaining the cap portion (22) of a plunger (20) therein. The body member (54) is moveable for drawing the plunger (20) of the barrel (14) to draw medicant into the barrel (14). A digital readout display is operatively connected to the body member (54) for projecting a digital output quantitating the amount of fluid drawn into the barrel (14) by movement of the plunger (20) axially out from the barrel (14).

12 Claims, 3 Drawing Sheets

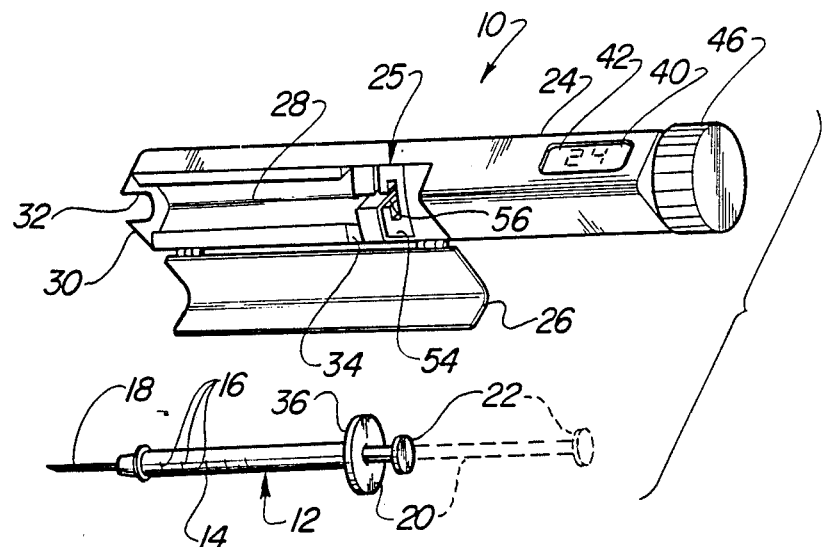
Fig-3
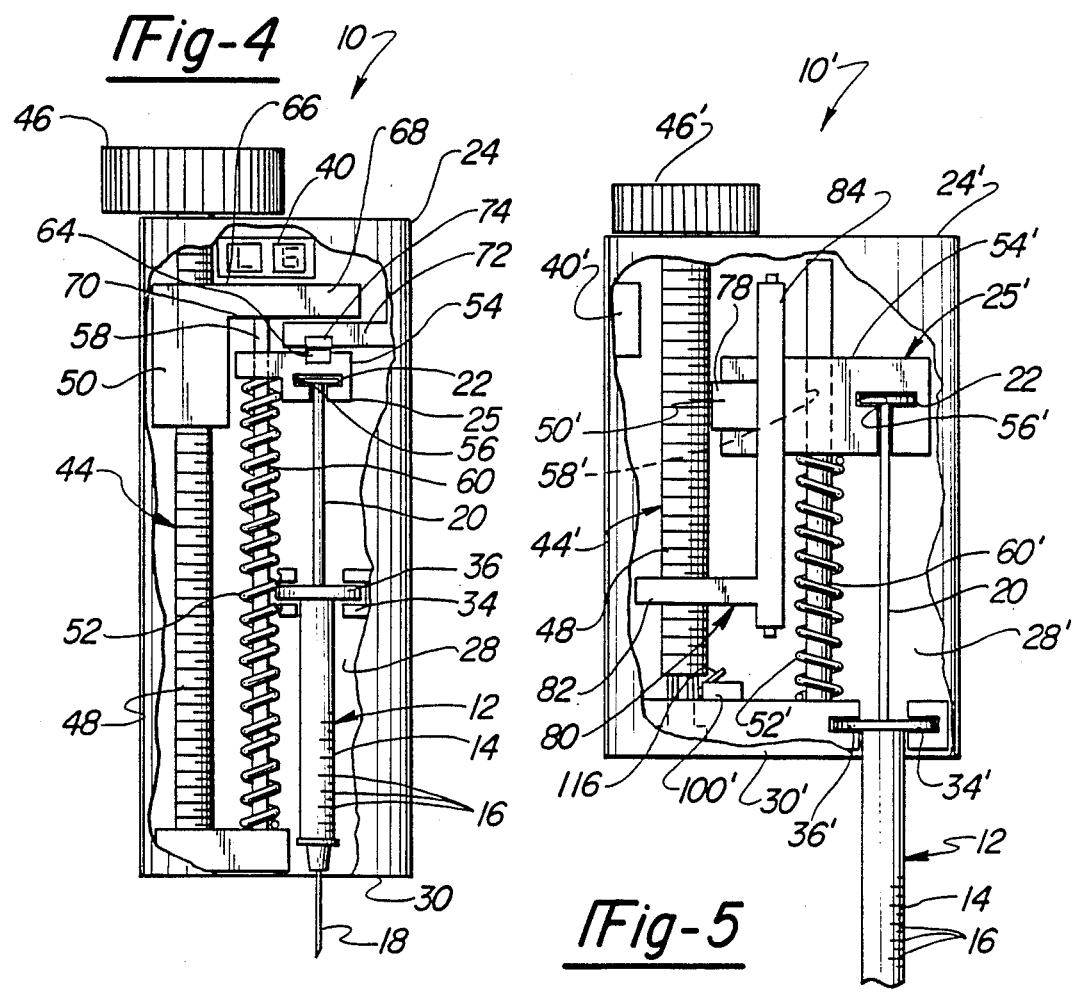
Fig-4
Fig-5

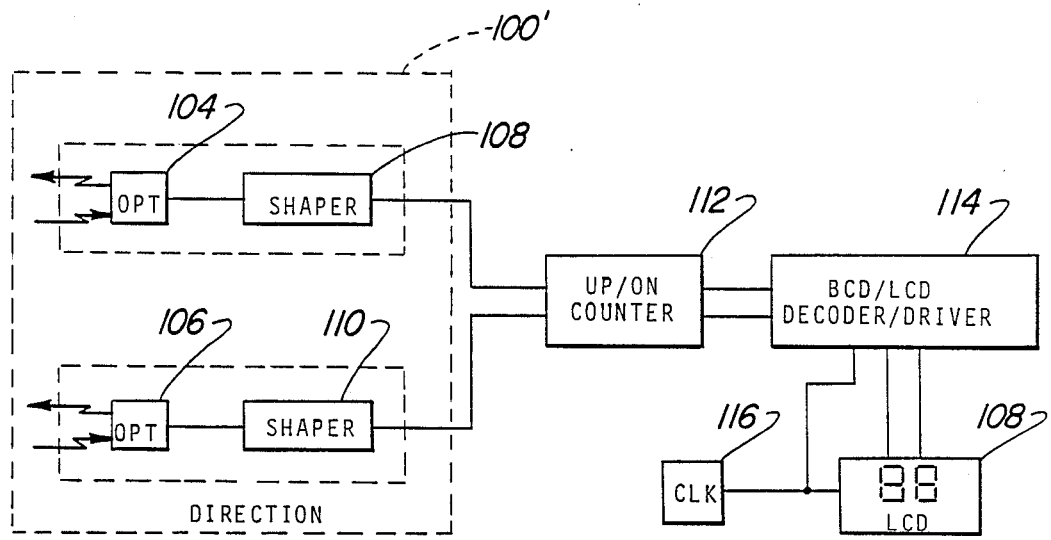
Fig-6
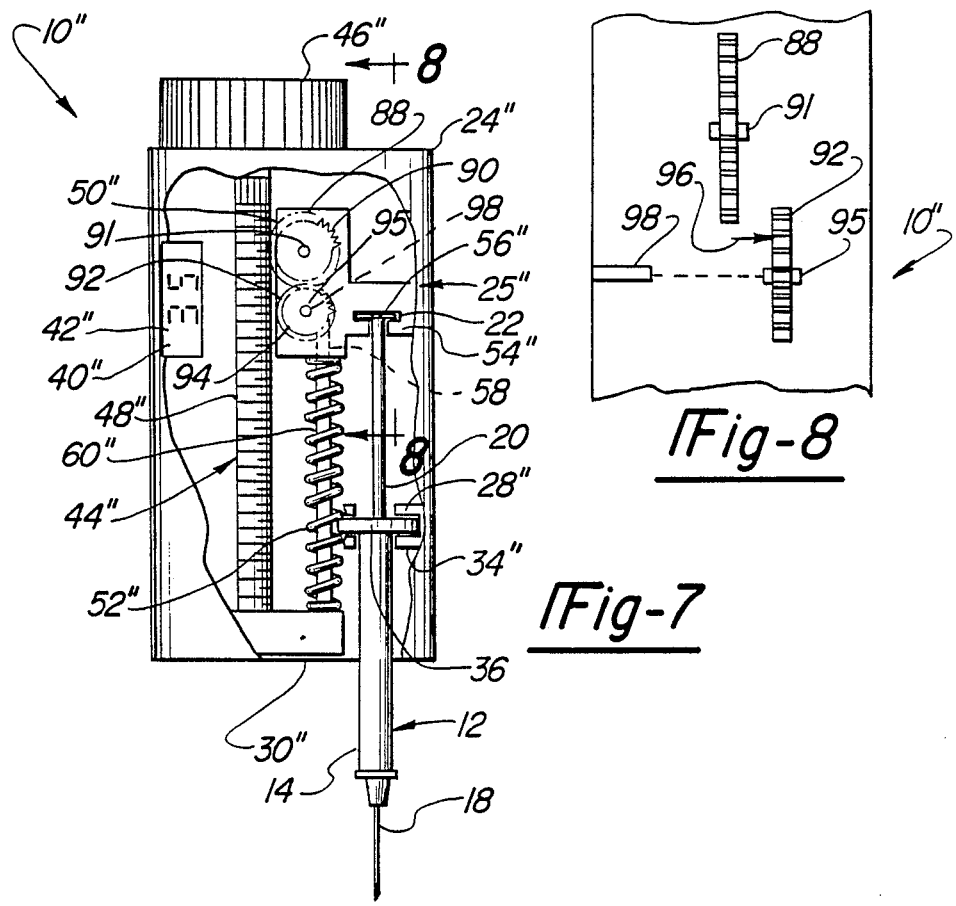
Fig-7
Fig-8

DIGITAL DISPENSER

TECHNICAL FIELD

This invention relates to a filling aid for a medicant syringe to assist the user in the filling of the syringe, and more particularly, to a device for use by persons who self-administer medicant by means of a syringe, as a safety device to insure proper exact filling of the syringe.

BACKGROUND ART

Currently in the United States there are tens of millions of parenteral medications dispensed each year. Because of the sheer numbers and the repetitious nature of giving parenteral medication, errors in dosages unavoidably occur. Dosage errors result in complications, as well as deaths. Additionally, the number of people who self-administer parenteral medications has greatly increased in the past few years.

Devices have been developed to aid in the filling of and injection by syringes. U.S. Pat. No. 3,965,945 to Ross, issued June 29, 1976 discloses a preadjustable device to which a medicant syringe may be attached for the filling of the syringe with medicant. The device includes an over fill control to allow for a slight overfill of the syringe and the subsequent expelling of the overfilled medicant and entrapped air. The device includes a means for holding a syringe and a threaded shaft actuator in the form of a screw. The device includes no means to assist in the reading of the analogue indications on the syringe. That is, there are no means provided to assist the user in visualizing the amount of medicant drawn into the syringe barrel. This is a considerable problem with patients who self-administer drugs because such patients, such as diabetics, have poor eyesight.

The U.S. Pat. No. 4,261,358 to Vargas et al, issued Apr. 14, 1981 discloses an automatic syringe plunger. This device does not include any means for assisting the user in determining the amount of medicant drawn into the syringe.

The aforementioned patents are examples of prior art automatic syringe plungers, all of which having the problem of not assisting the user in visualizing the amount of medicant drawn into the syringe. The present invention addresses the aforementioned problem by providing a device for automatically dispensing parenteral medications using digital rather than analog systems to indicate clearly to the patient the amount of medicant drawn into the barrel of the syringe.

SUMMARY OF THE INVENTION

In accordance with the subject invention there is provided a device of the type for use with a syringe including a barrel for containing the medicant therein and supporting a needle thereon and a plunger having one end operatively disposed within the barrel and a second end including a cap portion, the device including housing means having a chamber defining an axis and a base portion, and barrel holder means fixedly mounted within the housing means for holding the barrel of the syringe in a position parallel to the axis while exposing the needle from the housing means. Plunger holder means is mounted within the housing means and movable therein along the axis relative to the barrel holder means for holding the plunger and moving the plunger axially relative to the barrel. The device is characterized by including digital readout means operatively connected to the plunger holder means for projecting a digital output quantitating the amount of fluid drawn into the barrel by movement of the plunger axially away from the base portion.

FIGURE IN THE DRAWINGS

Other advantages of the present invention will be readily appreciated as the same becomes better understood by reference to the following detailed description when considered in connection with the accompanying drawings wherein:

FIG. 3 is a perspective view of the present invention;

FIG. 4 is a side elevational view of the present invention partially broken away;

FIG. 5 is a side elevational view of a second embodiment of the present invention partially broken away;

FIG. 6 is a schematic flow diagram of the circuitry of the second embodiment of the present invention;

FIG. 7 is a side elevational view partially broken away of a third embodiment of the present invention; and FIG. 8 is a cross sectional view taken substantially along lines 8—8 of FIG. 7.

DETAILED DESCRIPTION OF THE DRAWINGS

Figure 1:
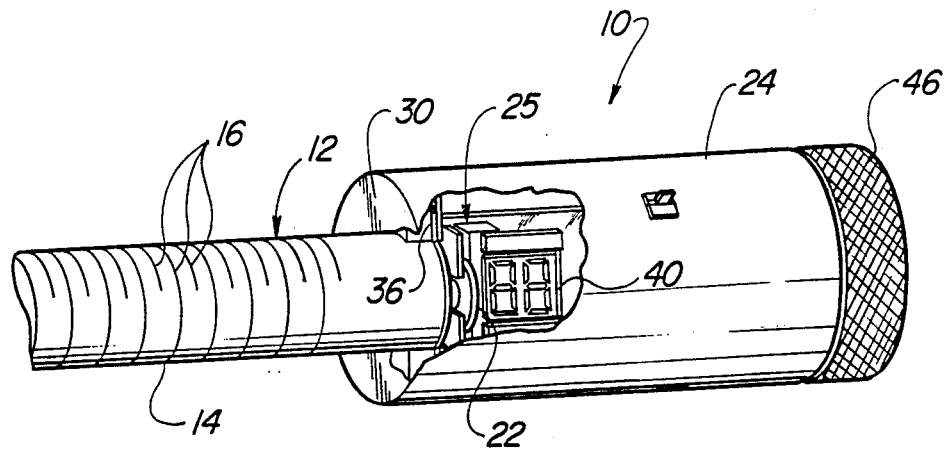
FIG. 1 is a perspective view of a device constructed in accordance with the subject invention, partially broken away.

An aid device constructed in accordance with the present invention is generally shown at 10 in the drawings. Like elements of the several embodiments shown in the drawings are indicated by like primed numbers.

The aid device constructed in accordance with the present invention is for use with a syringe generally indicated at 12. The syringe 12 is typically disposable of the type that includes a barrel 14 generally made of a clear or translucent plastic material. The barrel 14 includes a plurality of standard analog markings 16 normally used to quantitate the amount of medicant drawn into the syringe. The barrel 14 also includes an annular flange 36 extending radially outwardly therefrom. A needle 18 is supported at one end of the barrel 14. A plunger 20 has one end disposed within the barrel 14 and second end including a cap portion 22.

The present invention includes a housing 24. The housing 24 may take on a plurality of shapes, and is shown in the Figures as an oblong barrel shaped housing. The housing 24 includes a cover member 26 hingedly connected thereto. The housing 24 defines a chamber 28 therein for containing the barrel 14 and plunger 20 of a syringe 12. The cover 26 has a closed condition wherein it encloses the syringe 12 within the chamber 28.

The chamber 28 along its length defines a longitudinal axis of the housing 24. The housing further includes a base portion 30. The base portion 30 includes a slot 32 therethrough for allowing the needle 18 to extend therethrough.

The device 10 includes barrel holder means in the form of recess 34 fixedly mounted within the housing 24 for holding the barrel 14 of the syringe 12 in a fixed position parallel relative to the axis of the housing 20 while exposing the needle 18 from the housing 24. The radially outwardly projecting flange 36 which is seated within the recess 34 and thereby fixedly retained therein when the cover 26 is closed. Closing of the cover 26 prevents the flange 36 from moving outward from the recess 34.

Generally, the invention includes plunger holder means 25 mounted within the housing 24 and movable therein along a line parallel to the aforementioned axis of the chamber 28 relative to the fixed recess 34 for holding the plunger 20. The plunger holder means 25 can move the plunger 20 axially relative to the fixed barrel 14. The plunger 20 is withdrawn from the barrel 14 to draw medicant into the barrel 14 and forced into the barrel 14 to eject medicant therefrom. The invention is characterized by digital readout means operatively connected to the plunger holder means 25 for projecting a digital output quantitating the amount of medicant drawn into the barrel 14 by movement of the plunger 20 axially away from the base portion 30. That is, the plunger is moved or drawn out of the barrel 14 by the plunger holder means to draw medicant into the barrel 14, the plunger holder means being operatively connected to a digital readout means which projects a digital or synthetized voice output quantitating the amount of fluid drawn into the barrel 14. Thusly, the invention provides an easy and accurate means for a patient having poor eye sight to interpret the amount of medicant drawn into the barrel without having to read analog markings 16 on the barrel 14.

More specifically, and as shown in the drawings, the digital readout means can include a numerical LED or LCD display 40 shown through an opening 42 in the housing 24. Alternatively, the digital readout means could include a sound projecting digital display indicating the digital display verbally, such a voice output being well suited for visually impaired users.

The device 10 includes actuator means operatively connected to the plunger holder means 25 for moving the plunger holder means 25 relative to the barrel holder means 34. The actuator means includes a vernier screw generally indicated at 44 having a head portion or a thumb screw portion 46 disposed outside the housing 24 and a threaded portion 48 extending parallel to the axis of the chamber 28. The plunger holder means 25 includes a follower 50 threadedly connected to the threaded portion 48 for operatively connecting the plunger holder means 25 to the threaded portion 48 whereby turning of the thumb screw 46 in one direction moves the plunger holder means 25 away from the base portion 30 for drawing the plunger 20 from the barrel 14 and drawing medicant into the barrel 14. Turning of the thumb screw 46 moves the plunger holder means 25 away from the base portion 30 thereby drawing the plunger 20 out from the barrel 14 and drawing medicant into the barrel 14. The amount of medicant drawn into the barrel 14 is indicated by the digital display 40.

Spring 52 has one end connected to the base portion 30 and a second portion connected to the plunger holder means 25. The spring 52 biases the plunger holder means 25 towards the base portion 30 and against the drawing force of the follower 50 actuated by the thumb screw 46 and threaded portion 48 of the vernier screw 44.

The device 10 includes release means for operatively releasing the plunger holder means 25 from the connection to the threaded portion 48 of the vernier screw 44, the spring 52 then forcing the plunger holder means 25 towards the base portion 30 along the axis of the chamber 28 when the release means releases the follower 50 whereby the plunger 20 is forced into the barrel 14 to eject medication therefrom.

More specifically, the plunger holder means 25 includes a body member 54. The body member 54 includes a recessed portion 56 therein for containing the cap portion 22 of the plunger 20. The body member 54 also includes an opening 58 extending therethrough. The housing 24 includes a pin member 60 supported therein and extending in a direction parallel relative to the axis of the chamber 28. The pin member 60 extends through the opening 58 in the body member 54 for guiding the reciprocating movement of the body member 54. The body member 54 is capable of sliding along the pin member 60 either against the biasing force of the spring 52 as the body member 54 is operatively connected to the follower 50 by the release means, or to slide with the force of the spring 52 towards the base portion 30 when the release means releases the body member 54 from the follower 50. In other words, the body member 54 is operatively connected to the threaded portion 48 of the screw 44 through the follower 50 and release means. Upon being released from this operative connection to the threaded portion 48, the spring 52 is free to bias the body member 54 towards the base portion 30. Thus, the present invention provides an automatic device which aids the drawing of medicant into the barrel 14 of the syringe 12 as well as providing automatic injector means automatically forcing the plunger 20 into the barrel 14 to force medicant therefrom.

Figure 2:
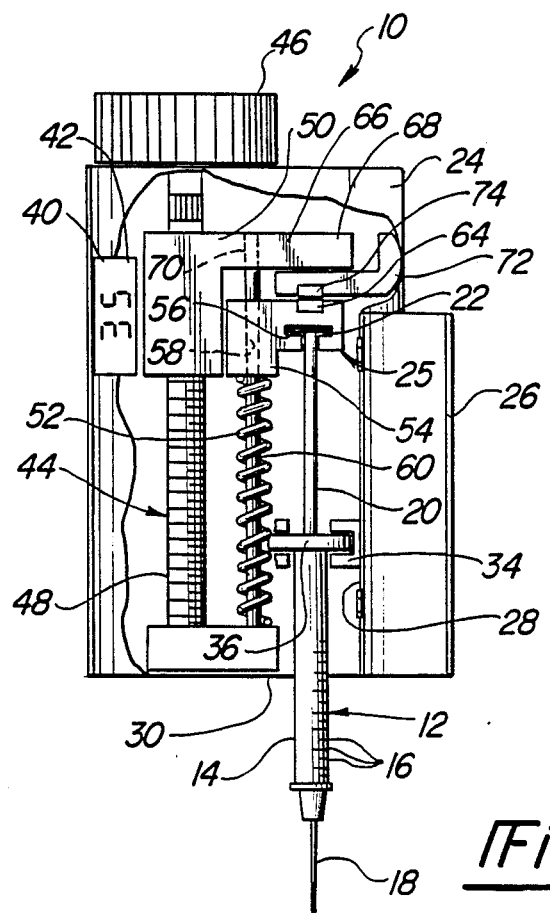
FIG. 2 is an elevational side view of the invention, partially broken away.

In the embodiment shown in FIGS. 2 and 4, the body member 54 includes a first magnet 64 mounted on its upper surface. The follower means includes a member 66 threadedly connected about the threaded portion 48 of screw 44 and having an arm 68 extending therefrom. The pin 60 has one end 70 extending through an opening in the arm 68, the pin 60 preventing rotation of the follower member 66 relative to the threaded portion 48 such that rotation of the threaded portion 48 moves the follower member 66 axially along the length of the threaded portion 48. A button member 72 is slideably mounted on the arm 68 and includes a second magnet 74 mounted thereon. The button member 72 is slideably connected to the arm 68 of the follower member 66 for selectably moving the second magnet 74 into and out of contact with the first magnet 64 whereby movement out of connect releases the body member 54 from the follower member 66 so as to be forced towards the base portion 30 by the spring 52.

In operation, a patient rotates the thumb screw 46 to move the follower member 66 away from the base portion 30 of the housing 24 thereby drawing the plunger 20 from the barrel 14 and drawing medicant into the barrel 14. The amount of medicant drawn into the barrel is indicated by the digital display 40. During the injection process, depression of the button 72 moves the second magnet 74 out of contact with the first magnet 64 thereby releasing the body member 54 from the follower member 66. The spring 52 forces the body member 54 towards the base portion 30 thereby forcing the plunger 20 into the barrel 14. Medicant is forced from the barrel 14 through the needle and into the patient.

A second embodiment of the present invention is shown in FIG. 5 and the circuitry therefore is shown in FIG. 6. The follower means 50' includes a finger member 78 mounted on the body member 54'. The finger member 78 is moveable into and out of engagement with the threaded portion 48' of the screw 44'. Various means can be used to pivotally connect the finger 78 to the body member 54'. The release means includes a lever member generally indicated at 80 which is operatively connected to the finger member 78 for selectively moving the finger 78 out of engagement with the threaded portion 48' thereby the biasing spring 52' forces the body member 54' to force the plunger 20 into the barrel 14.

The lever member 80 includes a handle portion 8 extending out through the housing 24' and a shaft portion 84 schematically shown in FIG. 5 as being pivotally connected to the housing 24'. Depression of the handle portion 82 pivots the shaft portion 84. The shaft portion 84 can be operatively connected to the finger 78, as by a cammed surface, to move or pivot the finger 78 out of or into engagement with the threaded portion 48'. Moving the handle 82 to disengage 78 can also interrupt a switch (not shown) operatively connected to the digital display 40 by means known in the art to reset the digital display 40 at zero.

In operation, turning of the thumb screw 46' forces the follower means 50' in the form of the finger 78 to be drawn along the axial length of the threaded portion 48' thereby moving the body member 54' away from the base portion 30'. Moving of the handle 82 pivotally rotates the shaft portion 84 which moves the finger 78 out of contact with the threaded portion 48'. Upon being released from the threaded portion 48', the spring 52' forces the body member 54' towards the base portion 30' and forces the plunger 20 into the barrel 14. Medicant is then forced from the barrel 14.

A third embodiment of the present invention is shown in FIG. 7. In this embodiment, the follower means 50" includes a first gear member 88 mounted on the body member 54". The first gear member 88 has a toothed radial outer periphery 90 engaging the threaded portion 44". The gear 88 rotates about a first axis of rotation. A second gear member 92 is mounted on the body portion 54" and has a toothed radial outer periphery 94 engaging the toothed periphery 90 of the first gear member 88. As shown in FIG. 8 by the arrow indicated at 96, the second gear member 92 is moveable axially along its second axes of rotation 95 into and out of engagement with the first gear member 88. Second gear member 92 is also rotatable in a single direction allowing rotation of the screw 44" to move the body member 54" from the base portion 30" when the first and second gears 88 and 92 are engaged. The release means includes a lever or button member 98 schematically shown to be operatively connected to the second gear 92 for moving the second gear member 92 axially along its second axis of rotation as indicated by the arrow 96 to disengage from the first gear member 88 thereby allowing the biasing spring 52" to force the body member 54" towards the base portion 30"

In operation, medicant is drawn into the barrel 44 as previously described by rotation of thumb screw 46". The engaged gears 88 and 92 prevent gear 88 from being rotated as the thumb screw 46" is rotated to withdraw medicant from the syringe. Upon injection, depression of the button 98 moves the gear 92 along its second axis 95 in the direction of the arrow 96 so as to disengage the first gear 88. The first gear 88 is then free to rotate in either direction so that the spring 52" is free to force the body member 54" towards the base portion 30" thereby forcing the plunger 20 into the barrel portion 14. Medicant is forced from the barrel portion 14 by the plunger 20.

FIG. 6 shows a schematic flow diagram of the circuitry of the subject invention. The device shown at 10' in FIG. 5 illustrates the components comprising the circuitry. A sensor, magnetic or optical, is indicated at 100'. The sensor senses information about the amount of rotation and direction of rotation of the screw 44'. A micro switch lever 116 is operatively connected to the sensor 100. The lever 116 opens and closes a micro switch by being depressed. When the micro switch 116 is closed, the digital display 40 as actuated through the sensor 100 is operational. When the micro switch 116 is open, the digital display 40' is nonoperational. The digital display 40' is zeroed when the micro switch 116 is open, the digital display being nonoperational. Thus, the switch is set at zero and the micro switch 116 can be closed and again made operational. Thusly, the digital display 40' can be used to assist first drawing up an amount of a first medicant. After the proper amount of the first medicant has been drawn into the barrel 44 as indicated by the digital display 40', the micro switch/lever 116 is depressed the micro switch thereby zeroing the digital display 40'. The micro switch is then closed once again. A known amount of a second medicant can be drawn into the barrel 14 as indicated by the digital display. Hence, the body member 54 need not be released in order to zero the digital display 40. Thusly, a patient need not mentally add amounts of different medicants to be drawn into the barrel 14 but rather the digital display can be used to quantitate separately and sequentially different amounts of different medicants.

The body member 54' contacts and depresses the lever 116 upon being released to reset the digital display 40 upon injection of the medication from the syringe 12. Specifically, the body member 54' has an undersurface 118 which contacts and deflects the switch lever 116 when the body member 54' is released and biased completely to the switch lever 116 by spring 52'. Thusly, the mechanical and digital mechanisms are simultaneously reset to zero.

As shown in the flow diagram in FIG. 6, the sensor means 100' is shown as the combination of an optical sensor 104 for counting rotations of the screw 44 and at 106 for sensing the direction of rotation. The flow chart further provides translation means for translating the sensed information from the sensor means 104, 106 into digital information communicated to the digital readout means shown as an LED at 108 in FIG. 6.

More specifically, the sensor means 100' includes the first optical sensor 104 for optically sensing the amount of rotation of the screw and providing a first output wave signal. The sensor means 100' further includes a second optical sensor 106 for optically sensing the direction of rotation of the screw and providing a second output wave signal. The translation means includes first and second shaper circuits 108, 110 for shaping the first and second output signals, respectfully. A counter 112 quantitates the shaped output waves. A decoder/driver 114 decodes the quantitated waves for transmission by the digital output 108.

The present invention can have utility at hospital pharmacies and nursing units where pharmacies may prepare hundreds of injections per day. The present invention can be used in the preparation of such injections. In particular, a large, easy to read digital display would be advantageous to diabetics for whom failing eyesight is a common complication of their disease.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An aid device (10) of the type for use with a syringe (12) including a barrel (14) for containing a medicant therein and supporting a needle (18) thereon and a plunger (20) having one end operatively disposed within the barrel (14) and a second end including a cap portion (22), said device (10) comprising: housing means (24) including a chamber (28) having a length defining an axis, said housing means (24) having a base portion (30); barrel holder means (34) fixedly mounted within said housing means (24) for holding the barrel (14) of the syringe (12) in a fixed position parallel to said axis while exposing the needle (18) from said housing means (24); plunger holder means (25) mounted within said housing (24) and movable therein along said axis relative to said barrel holder means (34) for holding the plunger (20) and moving the plunger (20) axially relative to the barrel (14); digital readout means operatively connected to said plunger holder mean s (25) for projecting a digital output quantitating the amount of medicant drawn into the barrel (14) by movement of the plunger (20) axially away from the base portion (30); actuator means operatively connected to said plunger holder means (25) for moving said plunger holder means (25) relative to said barrel holder means (34), said actuator means including a vernier screw (44) having a head portion (46) disposed outside of said housing means (24) and a threaded portion (48) extending parallel relative to said axis, said plunger holder means (25) including follower means (50) threadedly connected to said threaded portion (48) for operatively connecting said plunger holder means (25) to said threaded portion (48) whereby turning of said head portion (46) in one direction moves said plunger holder means (25) away from said base portion for drawing the plunger (20) from the barrel (14) and drawing medication into the barrel (14); and release means for operatively releasing said plunger holder means (25) from said threaded portion (48) and biasing means (52) for forcing said plunger holder means (25) towards said base portion (30) along said axis when said release means releases said plunger holder means (25) whereby the plunger (20) is forced into the barrel (14) to eject medication therefrom.

2. An aid device as set forth in claim 1 further characterized by said digital readout means including a numerical LED or LCD digital display (40).

3. An aid device as set forth in claim 1 further characterized by said digital readout means including a sound projecting digital display.

4. An aid device as set forth in claim 1 further characterized by said plunger holder means (25) including a body member (54) having a recessed portion (56) therein containing the cap portion (22) of the plunger (20) and an opening (58) extending therethrough, said housing means (24) including a pin member (60) supported therein and extending parallel relative to said axis, said pin member (60) extending through said opening (58) for guiding the reciprocating movement of said body member (54) towards and away from said base portion (30), said body member (54) being operatively connected to said release means for being operatively released from said follower means (50), said biasing means (52) being connected between said housing means (24) and said body member (54) for applying a biasing force on said body member (54) when said body members (54) is operatively released from said threaded portion (48).

5. An aid device as set forth in claim 4 further characterized by said follower means (50') including a finger member (78) mounted on said body member (54') and being moveable into and out of engagement with said threaded portion (48'), said release means including a lever member (80) operatively connected to said finger member (78) for selectively moving said finger member (78) out of engagement with said threaded portion (48') whereby said biasing means (52') forces said body member (54') to force the plunger (20) into the barrel (14).

6. An aid device as set forth in claim 5 further characterized by said lever member (80) including a handle (82) extending out of said housing means (24') and a shaft portion connected to said handle and operatively connected to said finger member (78), said shaft portion (84) being pivotally connected to said housing means (24'), depression of said handle (82) pivoting said shaft portion (84) to move said finger members (78) out of engagement with said threaded portion (48').

7. An aid device as set forth in claim 4 further characterized by said body member (54) including a first magnet (64) therein and said follower means (50) including a second magnet (74) for magnetically connecting said body member to said follower means (50), said release means including a button member (72) slideably connected to said follower means (50) for selectively moving said second magnet (74) into and out of contact with said first magnet (64) whereby movement out of contact releases said body member (54) from said follower means (50).

8. An aid device as set forth in claim 4 further characterized by said follower means (50") including a first gear member (88) mounted on said body member (54") and having teeth engaging said threaded portion (44") and a first axis of rotation (91) and a second gear member (92) mounted on said body portion (54") and having a toothed radially outer periphery (94) engaging said toothed periphery (90) of said first gear member (82) and a second axis of rotation (95), said second gear member (92) being movable axially along said second axis of rotation (95) into and out of engagement with said first gear member (88) and being rotatable in only a single direction allowing rotation of said screw (44") to move said plunger holder means (25") in relation to said base portion (30") when said first and second gears (88, 92) are engaged, said first gear member (88) being rotatable in either direction about said first axis of rotation (88), said release means including a lever (98) extending out of said housing means (24") and operatively connected to said second gear member (92) for moving said second gear member (92) axially along said second axis of rotation (95) to disengage said second gear member (92) from said first gear member (88) allowing said biasing means (52") to force said body member (54") towards said base portion (30").

9. An aid device as set forth in claim 4 further characterized by including sensor means (104, 106) for sensing information about the amount of rotation and direction of rotation of said screw (44) and translation means for translating said sensed information from said sensor means (104, 106) into digital information communicated to said digital readout means (109).

10. An aid device as set forth in claim 9 further characterized by said sensor means including first optical sensor means (104) disposed adjacent to said vernier screw for optically sensing the amount of rotation of said screw and providing a first output wave signal and second optical sensor means (106) disposed adjacent said screw for sensing direction of rotation of said screw and providing a second output wave signal, said translator means including first and second shaper means (108,110) for shaping the first and second output signals respectively and a counter (112) for quantitating the shaped output waves and decoder/driver means (114) for decoding said quantitated waves for transmission by said digital readout means (108).

11. An aid device as set forth in claim 10 further characterized by said sensor means (100') being mounted on said base portion (30') and including a deflectable switch lever (116) extending therefrom, said switch lever (116) being operatively connected to said sensor means (100') for resetting said digital read out means upon being deflected, said body member (54') having an under surface (118) which contacts and deflects said switch lever (116) when said body member (54') is biased and moved completely to said base portion (30') and released by said releasing means.

12. An aid device as set forth in claim 4 further characterized by said housing means (24) including a cover (26) hingedly connected thereto and having a closed condition wherein said cover (26) is disposed over said chamber (28) for retaining the barrel (14) of the syringe (12) within said chamber (28) and the cap portion (22) within said recessed portion (56) and an open condition exposing said chamber (28) allowing removal of the syringe (12) from said chamber (28).

* * * * *